US00PP24165P2

(12) United States Plant Patent
Verduin

(10) Patent No.: US PP24,165 P2
(45) Date of Patent: Jan. 14, 2014

(54) ***ASTILBE* PLANT NAMED 'HIP HOP'**

(50) Latin Name: ***Astilbe* hybrid**
Varietal Denomination: Hip Hip

(76) Inventor: Henricus Gijsbertus Johannes Verduin, Heemskerk (NL)

( * ) Notice: Subject to any disclaimer, the term of this patent is extended or adjusted under 35 U.S.C. 154(b) by 77 days.

(21) Appl. No.: 13/506,932

(22) Filed: May 25, 2012

(51) Int. Cl.
*A01H 5/00* (2006.01)

(52) U.S. Cl.
USPC ..... Plt./407; Plt./263.1

(58) Field of Classification Search
USPC ..... Plt./263.1, 407
See application file for complete search history.

*Primary Examiner* — Susan McCormick Ewoldt
(74) *Attorney, Agent, or Firm* — Penny J. Aguirre

(57) ABSTRACT

A new cultivar of *Astilbe* named 'Hip Hop' that is characterized by its densely branched foliage, its flowers with white-pink petals and sepals with dark red-purple pistil styles, its upright flower spikes, its growth habit that will produce a strong, well-developed plants with healthy foliage in one growing season, and its tolerance to heat, dry soils, and sunlight than is typical of many cultivars of *Astilbe*.

2 Drawing Sheets

Botanical classification: *Astilbe* hybrid.
Varietal denomination: 'Hip Hop'.

BACKGROUND OF THE INVENTION

The present invention relates to a new and distinct cultivar of *Astilbe* of hybrid origin and will be referred to hereafter by its cultivar name, 'Hip Hop'. 'Hip Hop' represents a new *Astilbe*, an herbaceous perennial grown for landscape use.

The new cultivar of *Astilbe* arose from a breeding program conducted by the Inventor in Heemskerk, The Netherlands. The female parent, an unnamed plant from the Inventor's breeding program, was pollinated by open pollination in 2004 with other unanmed plants from the Inventor's breeding program present in the breeding area. The specific male parent is therefore unknown. 'Hip Hop' was selected in June of 2006 from amongst the resulting seedlings.

Asexual reproduction of the new cultivar was first accomplished by division in Heemskerk, The Netherlands in February 2007. It has been determined that the characteristics of the new cultivar are stable and are reproduced true to type in successive generations.

SUMMARY OF THE INVENTION

The following traits have been repeatedly observed and represent the characteristics of the new cultivar as observed in trials in Heemskerk, The Netherlands and in combination distinguish 'Hipe Hop' as a unique cultivar of *Astilbe*.

1. 'Hip Hop' exhibits densely branched foliage.
2. 'Hip Hop' exhibits flowers with white-pink petals and sepals with dark red-purple pistil styles.
3. 'Hip Hop' exhibits upright flower spikes.
4. 'Hip Hop' exhibits healthy foliage.
5. 'Hip Hop' exhibits a growth habit that will produce a strong, well-developed plant in one growing season.
6. 'Hip Hop' has shown more tolerance to heat, dry soils, and sunlight than is typical of many cultivars of *Astilbe*.

The female parent of 'Hip Hop' differs from 'Hip Hop' in having flowers that are red-purple in color (petals, sepal and pistils). 'Hip Hop' can be most closely compared to the cultivars: 'Flamingo' (U.S. Plant Pat. No. 12,664) and 'Spotlight' (U.S. Plant Pat. No. 21,918). 'Flamingo' differs from 'Hip Hop' in having inflorescences that are broader with drooping tips, in having a lighter, musty fragrance, and in having light red-purple petals and pistil styles that are lighter red-purple. 'Spotlight' differs from 'Hip Hop' in having flowers with light pink petals and darker pink sepals.

BRIEF DESCRIPTION OF THE PHOTOGRAPHS

The plants and plant parts in the photographs depict a one-year old plant of 'Hip Hop' as grown outdoors in a 3-liter container in Heemskerk, The Netherlands.

Figure 1:
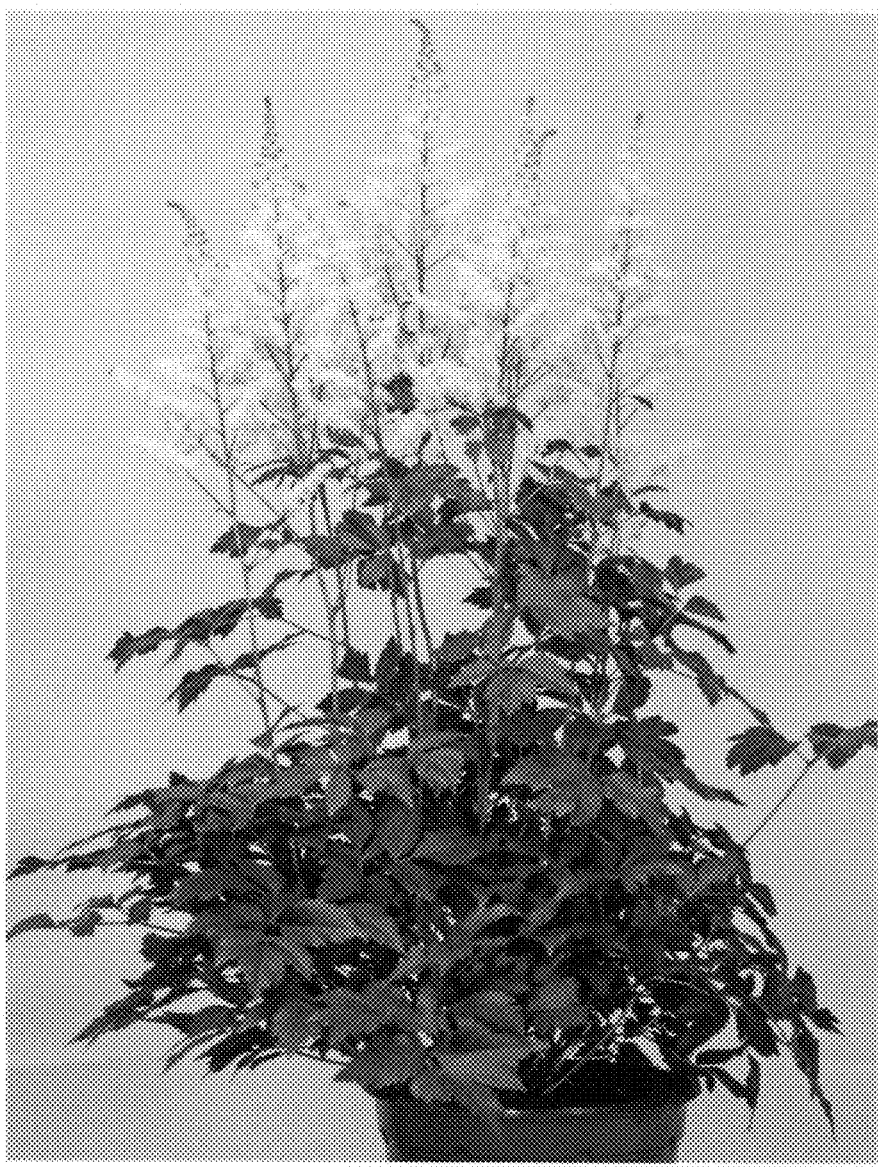

The photograph in FIG. 1 provides an overall view of the new *Astilbe* in bloom.

Figure 2:
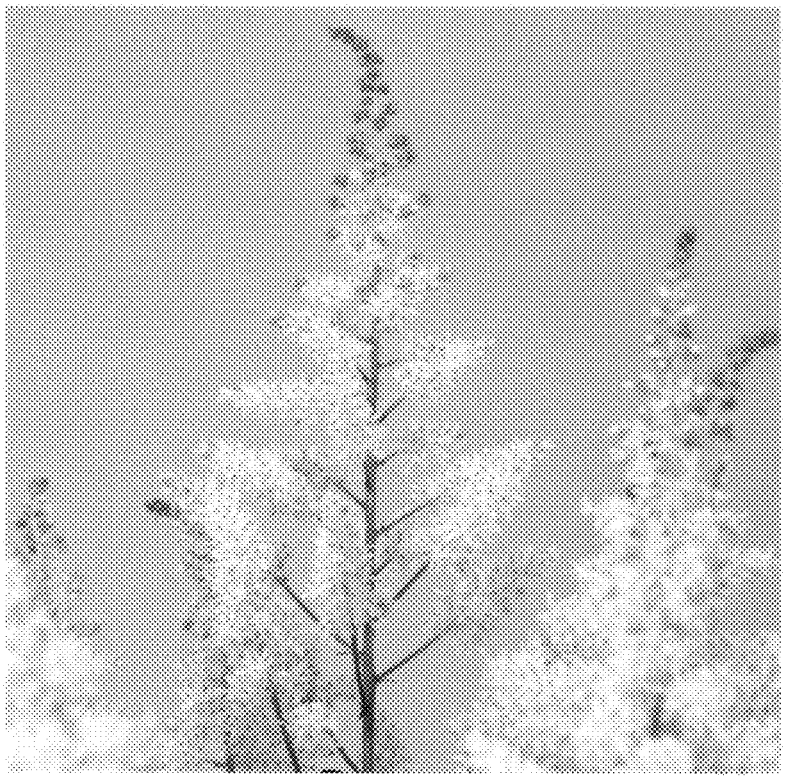

The photograph in FIG. 2 provides a close-up view of an inflorescence of 'Hip Hop'.

Figure 3:
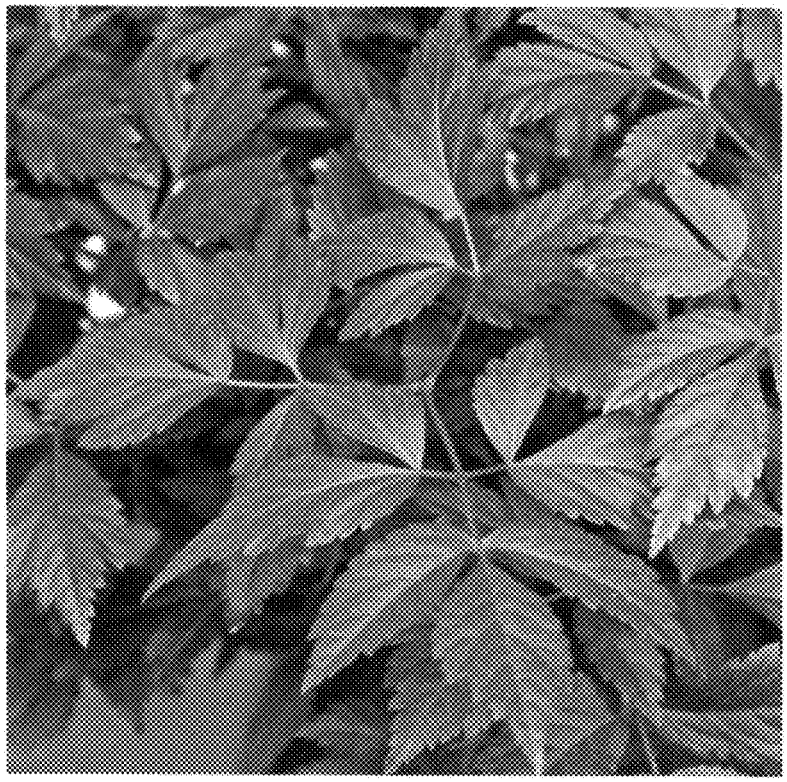

The photograph in FIG. 3 provides a close-up the foliage of 'Hip Hop'.

The colors in the photographs are as close as possible with the digital photography and printing techniques utilized and the color codes in the detailed botanical description accurately describe the colors of the new *Astilbe*.

DETAILED BOTANICAL DESCRIPTION

The following is a detailed description of one year-old plants as grown in a greenhouse in 3-liter containers in Heemskerk, The Netherlands. Plants were grown under average day temperatures ranging from 15° to 20° C. and average night temperatures ranging from 12° to 16° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Late spring through mid summer in The Netherlands.

*Plant type.*—Herbaceous perennial.
*Plant habit.*—Clump-forming, upright with blooms above branched healthy foliage.
*Height and spread.*—Average of 37.5 cm in height and 51.8 cm in spread.
*Hardiness.*—Known to be hardy at least to U. S. D. A. Zone 5.
*Environmentsl conditions.*—Has shown more tolerance to heat, dry soils, and sunlight than is typical of many cultivars of *Astilbe*.
*Diseases and pests.*—Similar medium density.
*Propagation.*—Stem division.
*Growth rate.*—Strong grower; producing a well-developed plant in one season.

Stem description (flowering stems):
*Stem color.*—144A.
*Stem shape.*—Round.
*Stem size.*—Average of 32.9 cm in length and 2.5 mm in diameter (including peduncle).
*Stem quantity.*—Average of 13 main stems.
*Stem surface.*—Moderately glossy, bases of stems moderately covered with short hairs, average of 2 mm in length and 200A in color.
*Stem aspect.*—Very strong, mostly held upright.
*Branching habit.*—No lateral branches, stems grow from the base.

Foliage description:
*Leaf division.*—Compound.
*Leaf attachment.*—Petiolate.
*Leaf arrangement.*—Alternate.
*Leaf shape.*—Biternate.
*Leaf number.*—Average of 4 per lateral branch.
*Internode length.*—Average of 10.6 cm.
*Leaf size.*—Average of 17.2 cm in length and 16.1 cm in width.
*Leaflet quantity.*—Average of 15 per leaf.
*Leaflet shape.*—Elliptic.
*Leaflet base.*—Attenuate.
*Leaflet apex.*—Long acuminate.
*Leaflet venation.*—Pinnate, color of upper surface; 144A, color of lower surface; 144B.
*Leaflet margins.*—Biserrate.
*Leaflet size.*—Average of 4.1 cm in length and 2 cm in width.
*Leaflet surface.*—Upper and lower surfaces moderately glossy and sparsely covered with short strigose hairs an average of 0.5 mm in length and 157B in color.
*Leaflet color.*—Young foliage upper surface; 143A to 143B, young foliage lower surface; between 138B and 143C, mature foliage upper surface; between 139A and 147A, mature foliage lower surface; between N137B and 147B.
*Petioles.*—Leaf; average of 10 cm in length, 2 mm in diameter and 144B in color, glabrous surface, petiolules; average of 6 mm in length, 1 mm in diameter and 144B in color, glabrous surface.
*Stipules.*—Both sides of the leaf base have a dry leafy stipule, lanceolate in shape, average of 8 mm in length, 2 mm in width and N199B in color.

Flower description:
*Inflorescence type.*—Numerous single rotate shaped flowers arranged on pyramidal panicles.
*Inflorescence aspect.*—Upright and held above foliage.
*Inflorescence size.*—Average of 24.9 cm in height and 13.1 cm in width.
*Flower fragrance.*—Moderately strong, sweet and pleasant fragrance.
*Flower quantity.*—Average of 1,100 per inflorescence.
*Flower lastingness.*—Average of 10 days.
*Flower buds.*—Broadly ovate in shape, average of 2.5 mm in length and 1.75 mm in diameter, color; 62C to 62D, base 145A.
*Flower aspect.*—Upright, outward, and drooping.
*Flower shape.*—Rotate.
*Flower size.*—About 4 mm in depth and 7 mm in diameter.
*Petals.*—Average of 5, un-fused, oblanceolate in shape, margin is entire, apex is broad acute, upper and lower surface dull, color of upper and lower surface (opening and mature) is NN155D.
*Calyx.*—Campanulate, average of 2 mm in length and 3 mm in diameter.
*Sepals.*—5, ovate in shape, margin is entire, apex is acute, base is cuneate and fused, surface is smooth and dull, color of upper and lower surface when immature; 145B to 145D, color of upper and lower surface when mature; 155A, about 0.75 mm in width and 2 mm in length.
*Bracts.*—2, at base of secondary racemes, lanceolate in shape, 137C in color and strongly tinged with N186C on upper and lower surface, about 1 mm in width and 3 mm in length, attenuate apex, base fused to rachis, upper and lower surface glabrous.
*Peduncles.*—Average of 24.5 cm in length and 2 mm in diameter, held at 0° (straight upright), peduncles of secondary racemes; held at an average angle of 50°, an average of 2 cm and 1.5 mm in width, strong, color is 143B, glabrous surface.
*Pedicels.*—About 1 mm in length and 0.5 mm in width, held at an average angle of 50°, 150D in color, glabrous surface.

Reproductive organs:
*Gynoecium.*—2 Pistils, about 1.5 mm in length, stigma is club-shaped and 69B in color, style is about 1 mm in length and 64B in color, ovary is 155A in color.
*Androcoecium.*—About 10 stamens, anthers are ovate in shape, basifixed, about 0.2 mm in length and 161D in color, filaments are about 3 mm in length and N155C in color, pollen is very low in quantity and N155A in color.
*Seed and fruit.*—No seeds or fruit have been detected to date.

It is claimed:

1. A new and distinct cultivar of *Astilbe* plant named 'Hip Hop' as herein illustrated and described.

* * * * *